United States Patent
Hu et al.

(10) Patent No.: US 12,031,903 B2
(45) Date of Patent: Jul. 9, 2024

(54) DETECTION METHOD AND DETECTION DEVICE FOR TRACE GAS

(71) Applicant: University of Science and Technology of China, Hefei (CN)

(72) Inventors: Shuiming Hu, Hefei (CN); Jin Wang, Hefei (CN); Yu Sun, Hefei (CN)

(73) Assignee: University of Science and Technology of China, Hefei (CN)

( * ) Notice: Subject to any disclaimer, the term of this patent is extended or adjusted under 35 U.S.C. 154(b) by 295 days.

(21) Appl. No.: 17/614,763

(22) PCT Filed: Mar. 30, 2020

(86) PCT No.: PCT/CN2020/082019
§ 371 (c)(1),
(2) Date: Nov. 29, 2021

(87) PCT Pub. No.: WO2020/238386
PCT Pub. Date: Dec. 3, 2020

(65) Prior Publication Data
US 2022/0228977 A1    Jul. 21, 2022

(30) Foreign Application Priority Data
May 29, 2019  (CN) .......................... 201910456370.9

(51) Int. Cl.
*G01N 21/35* (2014.01)
*G01N 21/3504* (2014.01)
(Continued)

(52) U.S. Cl.
CPC ..... *G01N 21/3504* (2013.01); *G01N 33/0027* (2013.01); *G02B 26/0858* (2013.01);
(Continued)

(58) Field of Classification Search
CPC ........... G01N 21/3504; G01N 33/0027; G02B 26/0858
See application file for complete search history.

(56) References Cited

U.S. PATENT DOCUMENTS 5,528,040 A * 6/1996 Lehmann .................. G01J 3/42
356/439
5,903,358 A * 5/1999 Zare ........................ G01N 21/39
250/343

(Continued)

FOREIGN PATENT DOCUMENTS

| CN | 101644673 A | 2/2010 |
| CN | 102735643 A | 10/2012 |

(Continued)

OTHER PUBLICATIONS

Extended European Search Report for European Application No. 20813712.5, dated Dec. 9, 2022.

(Continued)

*Primary Examiner* — Hugh Maupin
(74) *Attorney, Agent, or Firm* — Wolf, Greenfield & Sacks, P.C.

(57) ABSTRACT

A detection method and detection system for a trace gas, the detection method comprising: providing a resonant cavity, a gas to be measured being filled inside of a cavity body of the resonant cavity; providing detection light rays having different frequencies, the detection light rays being incident to the inside of the resonant cavity from one end of the resonant cavity in the extending direction and exiting from the other end of the resonant cavity in the extending direction so as to obtain detection light rays carrying information of a trace gas to be measured, and the cavity body of the resonant cavity having a degree of freedom of expansion and retraction in the extending direction so that the longitudinal mode frequency of the resonant cavity matches the frequencies of (Continued)

the incident detection light rays; and according to the detection light rays that have different frequencies and that carry information of said trace gas, acquiring the molecular saturation absorption spectrum of said trace gas, and calculating the concentration of said trace gas. The detection system comprises: a laser generating device, the resonant cavity, a photoelectric detection device, a feedback control device and a scanning control device. At room temperature, detection light rays provided by a conventional laser are used to detect the concentration of a trace gas.

8 Claims, 5 Drawing Sheets

(51) Int. Cl.
 *G01N 33/00* (2006.01)
 *G02B 26/08* (2006.01)
(52) U.S. Cl.
 CPC .............. *G01N 2201/06113* (2013.01); *G01N 2201/0636* (2013.01)

(56) References Cited

U.S. PATENT DOCUMENTS

| | | | | |
|---|---|---|---|---|
| 9,267,880 | B1* | 2/2016 | Tan | G01J 3/00 |
| 2001/0003482 | A1* | 6/2001 | Zare | G01J 3/42 |
| | | | | 356/432 |
| 2003/0189711 | A1* | 10/2003 | Orr | G01J 3/42 |
| | | | | 356/484 |
| 2005/0052653 | A1* | 3/2005 | Fidric | G01N 21/39 |
| | | | | 356/437 |
| 2005/0073687 | A1* | 4/2005 | Morville | H01S 3/0064 |
| | | | | 356/437 |
| 2008/0111993 | A1* | 5/2008 | Miller | G01N 21/39 |
| | | | | 356/437 |
| 2010/0315642 | A1* | 12/2010 | Chow | G01N 21/39 |
| | | | | 356/432 |
| 2018/0156718 | A1* | 6/2018 | Fleisher | G01N 21/031 |
| 2018/0275049 | A1* | 9/2018 | Mazzotti | G01N 21/3504 |
| 2019/0271641 | A1* | 9/2019 | Koulikov | G01N 33/15 |
| 2019/0296519 | A1* | 9/2019 | Kassi | G01N 21/39 |
| 2019/0301933 | A1* | 10/2019 | Allison | G01N 21/636 |
| 2022/0065778 | A1* | 3/2022 | Katchanov | G01J 3/4412 |

FOREIGN PATENT DOCUMENTS

| | | |
|---|---|---|
| CN | 103884679 A | 6/2014 |
| CN | 105651703 A | 6/2016 |
| CN | 106483069 A | 3/2017 |
| CN | 109066283 A | 12/2018 |
| CN | 110160989 A | 8/2019 |
| WO | WO 2014/170828 A1 | 10/2014 |
| WO | WO 2017/055606 A1 | 4/2017 |

OTHER PUBLICATIONS

Gianfrani et al., Cavity-enhanced absorption spectroscopy of molecular oxygen. Journal of the Optical Society of America B. Dec. 1, 1999;16(12):2247-54.

International Search Report and Written Opinion for International Application No. PCT/CN2020/082019 mailed Jul. 8, 2020.

Chen et al., Trace Carbon Monoxide Detection with a Cavity Ring-Down Spectrometer. Spectroscopy and Spectral Analysis. 2015;35(4):971-4.

Tian-Peng et al., Cavity-Enhanced Saturation Spectroscopy of Molecules with sub-kHz Accuracy. Chinese Journal of Chemical Physics. 2019;32(1):107-12.

* cited by examiner

DETECTION METHOD AND DETECTION DEVICE FOR TRACE GAS

This application is a national stage filing under 35 U.S.C. § 371 of International Patent Application Serial No.: PCT/CN2020/082019, filed Mar. 30, 2020, which claims priority to Chinese Patent Application No. 201910456370.9, filed May 29, 2019, entitled "METHOD AND DEVICE FOR DETECTING TRACE GAS", filed on May 29, 2019 with the China National Intellectual Property Administration. These applications are incorporated herein by reference in their entirety.

FIELD

This application relates to the technical field of optical detection, and more specifically relates to a method and a device for detecting trace gases.

BACKGROUND

Molecular absorption spectroscopy (MAS) is a technique for measuring the concentration of the target gas, which is specifically performed by: measuring absorption lines of a certain target gas component in the gas to be tested, to obtain the absorbance of the target gas molecule, and using the corresponding relationship between the absorbance and the concentration of the tested target gas molecule, to obtain the concentration of the tested target gas in the gas to be tested.

At present, the commonly used molecular absorption spectroscopy technical is to measure the absorbance of a certain absorption line of the target gas molecule (isotope), which satisfies the Beer-Lambert relationship. The HITRAN database discloses dozens of the absorption parameters of the major atmospheric molecules and their isotopes. During the measurement, in order to avoid being affected by some effects, e.g., the laser light power drift, optical medium transmittance fluctuations, it is usually necessary to scan the wavelength and record the laser spectrum within a certain of wavelength range, so as to obtain a complete envelope of an isolated spectral line of the target molecule; and then integrate the envelope to get the area, and the concentration of the target gas is obtained.

However, the Doppler broadening width (full width at half maximum) of near-infrared transitions may reach hundreds of MHz under normal temperature or high temperature condition, even at low pressure. Due to the presence of other molecules (or isotopes) in the background gas, if the target molecules (isotope) have a low content or weak absorption line (that is, when the target gas is a trace gas), the spectral lines are easily covered by the absorption of other background gases. As a result, the absorption signal of the target line will be hidden in the background and unable to be extracted, resulting in an invalid measurement.

Therefore, in the existing technology, the method of measuring the saturated molecular absorption spectrum of the trace gas has been adopted, expecting to take advantage of the narrow spectral lines of the saturated molecular absorption spectroscopy, and that it will not be affected by the absorption of the background gas, so as to realize the measurement of the concentration of the gas to be tested. Nevertheless, it has found that by use of continuous wave lasers, the molecular transition cannot be saturated easily under normal temperature condition, so that the purpose of using conventionally continuous wave lasers to measure trace gases under normal temperature condition cannot be achieved.

SUMMARY

In order to solve the above technical problems, this application provides a method and a system for detecting trace gases, for detecting the concentration of a trace gas or its isotope, by using the Doppler free cavity enhanced saturated molecular absorption spectroscopy under normal temperature condition.

To achieve the above technical purpose, embodiments of this application provides the following technical solutions:

A method for detecting a trace gas comprises:

providing a resonant cavity, and filling cavity interior of the resonant cavity with a gas to be tested, wherein the gas to be tested contains a trace gas to be tested;

providing probe light with different frequencies, wherein the probe light enters into interior of the resonant cavity from one end of the resonant cavity in an extension direction of the resonant cavity, and exits from the other end of the resonant cavity in an extension direction of the resonant cavity, to capture probe light carrying information of the trace gas to be tested, the cavity of the resonant cavity has retractable degree of freedom in the extension direction of the resonant cavity, so that a frequency of a longitudinal mode of the resonant cavity matches a frequency of incoming probe light; and obtaining a saturated molecular absorption spectrum of the trace gas to be tested according to the probe light carrying information of the trace gas to be tested with different frequencies, and calculating the concentration of the trace gas to be tested in the gas to be tested according to the saturated molecular absorption spectrum of the trace gas.

Optionally, a laser light generating device, a resonant cavity, a photoelectric detection device, a feedback control device and a scan control device are comprised, wherein the cavity interior of the resonant cavity is configured to fill with a gas to be tested, wherein the gas to be tested contains a trace gas to be tested; and the cavity of the resonant cavity has retractable degree of freedom in the extension direction of the resonant cavity;

the laser light generating device is configured to provide probe light with different frequencies under control of the feedback control device, wherein the probe light enters into interior of the resonant cavity from one end of the resonant cavity in an extension direction of the resonant cavity, and exits from the other end of the resonant cavity in an extension direction of the resonant cavity, to capture the probe light carrying information of the trace gas to be tested;

the photoelectric detection device is configured to convert the probe light carrying information of the trace gas to be tested into detection information in an electrical signal form;

the scan control device is configured to record the detection information in an electrical signal form, and to control the laser light generating device to adjust frequency of outgoing probe light in a stepping manner; and the feedback control device is configured to control the frequency of the outgoing probe light from the laser light generating device to match with a frequency of a longitudinal mode of the resonant cavity.

Optionally, the resonant cavity comprises:

a shell, having an incoming end and an outgoing end which are arranged opposite to each other;

a first reflector located inside the shell and close to the incoming end side, wherein an anti-reflection film is provided at one side of the first reflector facing to the incoming end;

a second reflector located inside of the shell and close to the outgoing end side, wherein reflective surfaces of the first reflector and the second reflector are arranged opposite to each other; and a piezoelectric device arranged adjacent to the first reflector and/or arranged adjacent to the second reflector, wherein the piezoelectric device is configured to push the first reflector and/or the second reflector adjacent to the piezoelectric device to move according to a received control electrical signal, to provide the cavity of the resonant cavity with a retractable degree of freedom in the extension direction of the resonant cavity.

Optionally, the feedback control device comprises: a radio-frequency signal source, a phase detection device and a PID amplification device, wherein the radio-frequency signal source is configured to generate a sinusoidal radio-frequency signal;

the phase detection device is configured to convert the detection information in an electrical signal form into an error signal according to the sinusoidal radio-frequency signal; and the PID amplification device is configured to convert the error signal into a feedback locking signal, so that the frequency of the probe light exiting from the laser light generating device matches with the frequency of the longitudinal mode of the resonant cavity.

Optionally, the laser light generating device comprises a laser, a frequency modulation device, and a coupling lens, wherein the laser is configured to generate a laser light;

the frequency modulation device is configured to modulate the laser light generated by the laser according to the feedback locking information, to obtain probe light with a frequency matching with the frequency of the longitudinal mode of the resonant cavity; and the coupling lens is configured to couple the probe light and to allow the coupled probe light to enter into the resonant cavity.

Optionally, the frequency modulation device is an electro-optic modulator.

Optionally, the scan control device comprises an information storage device and a frequency scanning device, wherein the information storage device is configured to record the detection information in an electrical signal form; and the frequency scanning device is configured to generate a control electrical signal, and to transmit the control electrical signal to the laser.

Optionally, the scan control device is further configured to obtain a saturated molecular absorption spectrum of the trace gas to be tested according to recorded detection information in an electrical signal form, and to calculate the concentration of the trace gas to be tested in the gas to be tested according to the saturated molecular absorption spectrum of the trace gas.

Optionally, the photoelectric detection device comprises a lens matching module and a photoelectric detection module, wherein the lens matching module is configured to match the spatial pattern of a light field inside the photoelectric detection device; and the photoelectric detection module is configured to convert the probe light carrying information of the trace gas to be tested into the detection information in an electrical signal form.

It can be seen from the technical solution described above that embodiments of this application provide a method and a system for detecting a trace gas. In the method for detecting a trace gas, the gas to be tested is filled into the resonant cavity. On one hand, the resonant cavity enhances the laser power of the probe light entering into the resonant cavity to improve the saturation parameters of molecular transition of the trace gas to be tested, and on the other hand enhances the effective absorption range of the trace gas to be tested, so that the sensitivity for detecting the weak absorption of the trace gas to be tested is increased and the saturated molecular absorption spectrum of the trace gas to be tested is obtained, which realizes the purpose of detecting the concentration of a trace gas by using the probe light supplied by a conventional laser under normal temperature condition.

In addition, due to the Doppler-free broadening property of the saturated molecular absorption spectrum, the obtained saturated molecular absorption spectrum of the trace gas to be tested may be effectively separated from the absorption spectra of the background gas molecules in the gas to be tested, thereby eliminating the interference from the background gas, and realizing the detection of the trace gas to be tested. Since frequencies of the saturated absorption spectra of the different molecular isotopes are significantly different, the method for detecting the trace gas provided by the embodiment of this application is also particularly effective for detecting a molecule with a specific isotope.

BRIEF DESCRIPTION OF DRAWINGS

Hereinafter, in order to more clearly illustrate the technical solutions in the embodiments of the present disclosure or the existing technology, a brief introduction will be made to the drawings that need to be used in the description of the embodiments or the existing technology. It is obvious that the drawings described below are only some examples of the present disclosure and that for these skilled in the art, other drawings may also be derived from them without inventive effort.

DETAILED DESCRIPTION

Figure 1:
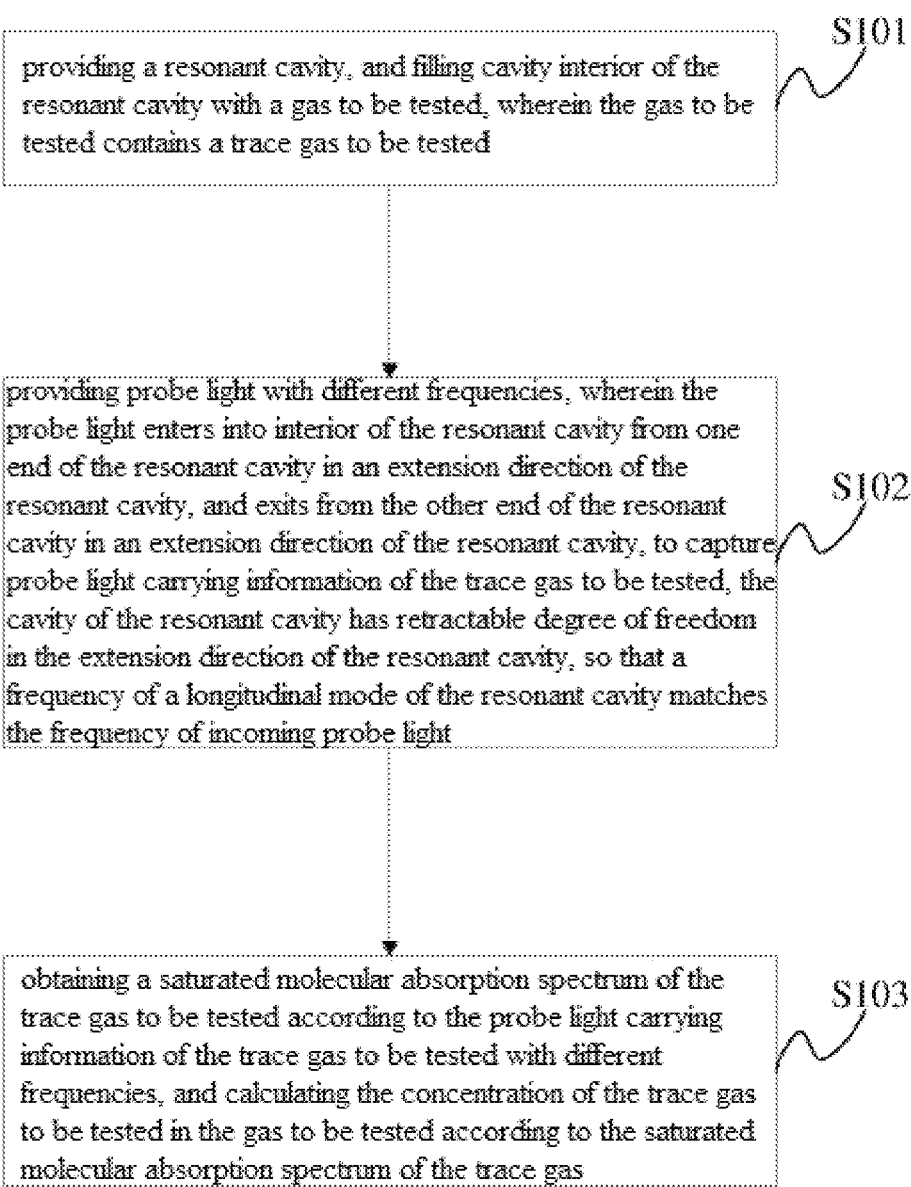
FIG. 1 is a schematic flow chart of a method for detecting a trace gas provided by an embodiment of this application.

As mentioned in the background, the commonly used laser absorption spectroscopy is to measure the absorbance of one absorption line of the target gas molecule (isotope), which satisfies the Beer-Lambert relationship:

$$T_v = I_v / I_0 = \exp(-k_v L);$$

wherein $T_v$ represents transmittance of a laser after going through optical path length L in a medium, $k_v$ is absorbance, which is a function of the concentration $X_{gas}$ of a measured target gas molecule, the absorption line intensity S(T) and the linear function φ(v) under the pressure of P, and the linear function satisfies ∫φ(v)dv=1, wherein v represents frequency. The absorbance $k_v$ may be expressed as:

$$k_v = S(T)X_{gas}P\varphi(v);$$

wherein φ(v) is the linear function obtained by convolution of the Gaussian Doppler broadening profile and the Lorentzian pressure broadening profile, and satisfies ∫φ(v) dv=1. The database HITRAN discloses the absorption line parameters of dozens of major atmospheric molecules and their isotopes (including center of spectral lines, S(T), etc.). During the measurement, in order to avoid being affected by the effects such as the laser light power drift, optical medium transmittance fluctuations, it is usually necessary to scan the wavelength and record the laser spectrum within a certain of wavelength range, so as to obtain a complete envelope of an isolated spectral line of the target gas molecule. By eliminating the influence of the linear function φ(v) in a manner of integral, the concentration of the target gas is obtained.

However, the Doppler broadening (full width at half maximum) of molecular near-infrared transitions may reach the level of hundreds of MHz under normal temperature or high temperature condition, even at low pressure. Due to the presence of other molecules (or isotopes) in the background gas, if the target gas molecules (isotope) have a low content or weak absorption line, the spectral lines are easily covered by the absorption of other background gases. As a result, the absorption signal of the target line will be hidden in the background and unable to be extracted, resulting in measurement failure.

A saturated molecular absorption spectrum is derived from the reduction of absorption signals measured by a probe beam resulted from a decreased number of molecules distributed in a lower state when an excitation beam with narrow linewidth excites some molecules to a higher state. In the case that the excitation beam and the probe beam have the same frequency but opposite directions, both of them only interact with molecules with zero lateral velocity, and an absorption dip free of Doppler broadening with a greatly-narrowed linewidth is called as the Lamb dip. Since the saturated molecular absorption spectrum generally has a linewidth narrower than the Doppler broadening by about three orders of magnitude, it will not be affected by the absorption of other background gases, thereby greatly improving the selectivity of detection.

The depth Δa of the saturated molecular absorption peak (Lamb dip) may be expressed by the following equation:

$$\Delta\alpha = \frac{a_m P_i}{\sqrt{1+S}} - \frac{a_m P_i}{\sqrt{1+2S}};$$

wherein $P_i$ is a partial pressure of a gas to be tested, $\alpha_m P$ is a absorption coefficient of a molecule to be tested without considering the saturation effect, S is a saturation parameter which is calculated by the following equation:

$$S = \frac{I}{I_s} = \frac{I}{I_{s0}\left[1+\left(\frac{\Gamma_P P}{\Gamma_T}\right)^2\right]};$$

wherein $I_s$ is a saturation power, $I_{s0}$ is a saturation power of a gas to be tested at the limit of zero pressure, $\Gamma_P$ is a pressure widening coefficient for depicting the relationship between the linewidth of a saturated molecular absorption spectrum and a gas pressure, $\Gamma_T$ is a widened transit time, and P is a total pressure of the sample gas. The area of lamb dip may obtained by the following equation:

$$A = \Delta\alpha \times \Gamma_{FWHF} = \alpha_m P_i(\Gamma_P P + \Gamma_T)\left(\frac{1}{\sqrt{1+S}} - \frac{1}{\sqrt{1+2S}}\right);$$

wherein $\Gamma_{FWHM}$ is the full width at half maximum of the Lamb dip. The concentration of the gas to be tested may be calculated according to the obtained area of the Lamb dip.

However, there are still lots of difficulties in using saturated molecular absorption spectra to detect trace molecules. The first is that the near-infrared vibrational and rotational transition moments of a molecule are very small, and the molecular transit broadening (about hundreds of kHz) is much larger than the natural broadening (even smaller than sub-Hz) under normal temperature condition, so that the transition only can be saturated at a very high laser power (above kW/cm²). The continuous wave semiconductor laser commonly used in gas detection cannot meet the requirements. Moreover, the saturated absorption is more greatly affected by the pressure broadening. In order to obtain a saturated absorption spectrum with sufficient contrast, the measurement needs to be performed at low pressure (10 Pa or lower), which requires a higher sensitivity of the measurement.

In view of that, an embodiment of this application provides a method for detecting a trace gas comprising:

providing a resonant cavity, and filling cavity interior of the resonant cavity with a gas to be tested, wherein the gas to be tested contains a trace gas to be tested;

providing probe light with different frequencies, wherein the probe light enters into interior of the resonant cavity from one end of the resonant cavity in an extension direction of the resonant cavity, and exits from the other end of the resonant cavity in an extension direction of the resonant cavity, to capture probe light carrying information of the trace gas to be tested, the cavity of the resonant cavity has retractable degree of freedom in the extension direction of the resonant cavity, so that a frequency of a longitudinal mode of the resonant cavity matches the frequency of incoming probe light; and obtaining a saturated molecular absorption spectrum of the trace gas to be tested according to the probe light carrying information of the trace gas to be tested with different frequencies, and calculating the concentration of the trace gas to be tested in the gas to be tested according to the saturated molecular absorption spectrum of the trace gas.

In the method for detecting a trace gas, the gas to be tested is filled into the resonant cavity. On one hand, the resonant cavity enhances the laser power of the probe light entering into the resonant cavity to improve the saturation parameters of molecular transition of the trace gas to be tested, and on the other hand enhances the effective absorption range of the trace gas to be tested, so that the sensitivity for detecting the weak absorption of the trace gas to be tested is increased and the saturated molecular absorption spectrum of the trace gas to be tested is obtained, which realizes the purpose of detecting the concentration of a trace gas by using the probe light supplied by a conventional laser under normal temperature condition.

In addition, due to the Doppler-free broadening property of the saturated molecular absorption spectrum, the obtained saturated molecular absorption spectrum of the trace gas to be tested may be effectively separated from the absorption spectra of the background gas molecules in the gas to be tested, thereby eliminating the interference from the background gas, and realizing the detection of the trace gas to be tested. Since frequencies of the saturated absorption spectra of the different molecular isotopes are significantly different, the method for detecting the trace gas provided by the embodiment of this application is also particularly effective for detecting a molecule with a specific isotope.

Hereinafter, the technical solutions in the embodiments of this application will be described clearly and completely, in conjunction with the drawings in the examples of this application. Obviously, the described embodiments are only part of the embodiments of this application, rather than all the embodiments. Based on the embodiments in this application, all other embodiments obtained by a person having ordinary skill in the art without creative labor should fall within the protection scope of this application.

As shown in FIG. 1, an embodiment of this application provides a method for detecting a trace gas comprising:

S101: providing a resonant cavity, and filling cavity interior of the resonant cavity with a gas to be tested, wherein the gas to be tested contains a trace gas to be tested;

S102: providing probe light with different frequencies, wherein the probe light enters into interior of the resonant cavity from one end of the resonant cavity in an extension direction of the resonant cavity, and exits from the other end of the resonant cavity in an extension direction of the resonant cavity, to capture probe light carrying information of the trace gas to be tested, the cavity of the resonant cavity has retractable degree of freedom in the extension direction of the resonant cavity, so that a frequency of a longitudinal mode of the resonant cavity matches the frequency of incoming probe light; and S103: obtaining a saturated molecular absorption spectrum of the trace gas to be tested according to the probe light carrying information of the trace gas to be tested with different frequencies, and calculating the concentration of the trace gas to be tested in the gas to be tested according to the saturated molecular absorption spectrum of the trace gas.

It should be noted that the trace gas refers to a gas component with very low component content (ppm level or lower) in a gas sample under a certain pressure. For example, carbon dioxide or methane and its isotope gas in the air may be considered as the trace gas.

Figure 2:
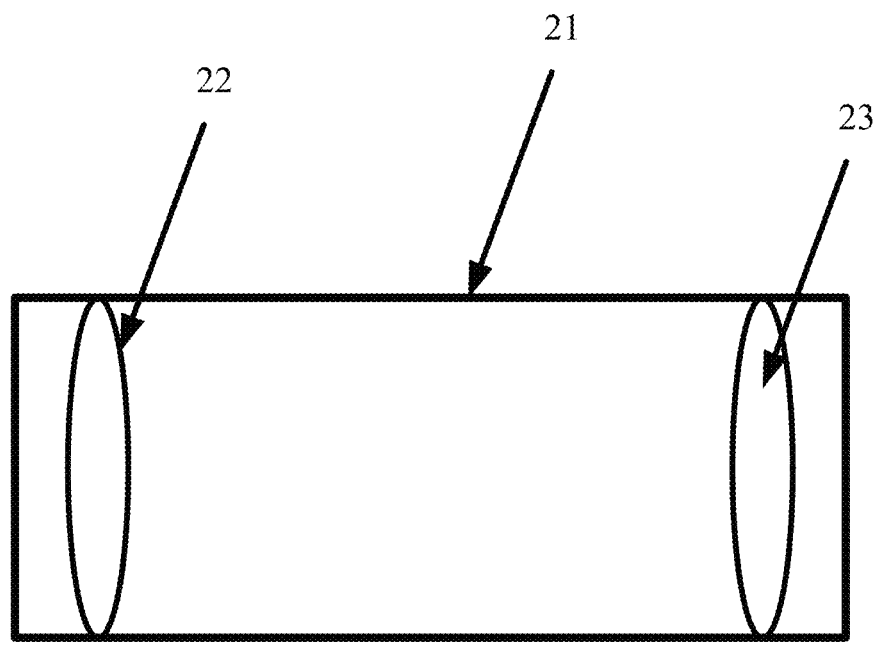
FIG. 2 is a schematic structure diagram of a resonant cavity provided by an embodiment of this application.

An example of this application provides a possible structure of the resonant cavity. Referring to FIG. 2, in this example, the resonant cavity includes a shell, a first reflector 22, a second reflector 23 and at least one piezoelectric device (not shown in FIG. 2) which are arranged in the shell 21, wherein the shell 21 comprises an incoming end and an outgoing end which are arranged opposite to each other; the first reflector 22 and the second reflector 23 are respectively arranged close to the incoming end and the outgoing end; and the reflective surface of the first reflector 22 and the second reflector 23 are opposite to each other; the first reflector 22 arranged close to the incoming end may be attached with an anti-reflection film at its side facing the incoming end, in order to increase the transmittance of incoming probe light.

In this example, in the method for detecting a trace gas, the gas to be tested is filled into the resonant cavity. On one hand, the resonant cavity enhances the laser power of the probe light entering into the resonant cavity to improve the saturation parameters of molecular transition of the trace gas to be tested, and on the other hand enhances the effective absorption range of the trace gas to be tested, so that the sensitivity for detecting the weak absorption of the trace gas to be tested is increased and the saturated molecular absorption spectrum of the trace gas to be tested is obtained, which realizes the purpose of detecting the concentration of a trace gas by using the probe light supplied by a conventional laser under normal temperature condition.

In addition, due to the Doppler-free broadening property of the saturated molecular absorption spectrum, the obtained saturated molecular absorption spectrum of the trace gas to be tested may be effectively separated from the absorption spectra of the background gas molecules in the gas to be tested, thereby eliminating the interference from the background gas, and realizing the detection of the trace gas to be tested. Since frequencies of the saturated absorption spectra of the different molecular isotopes are significantly different, the method for detecting the trace gas provided by the embodiment of this application is also particularly effective for detecting a molecule with a specific isotope.

Figure 3:
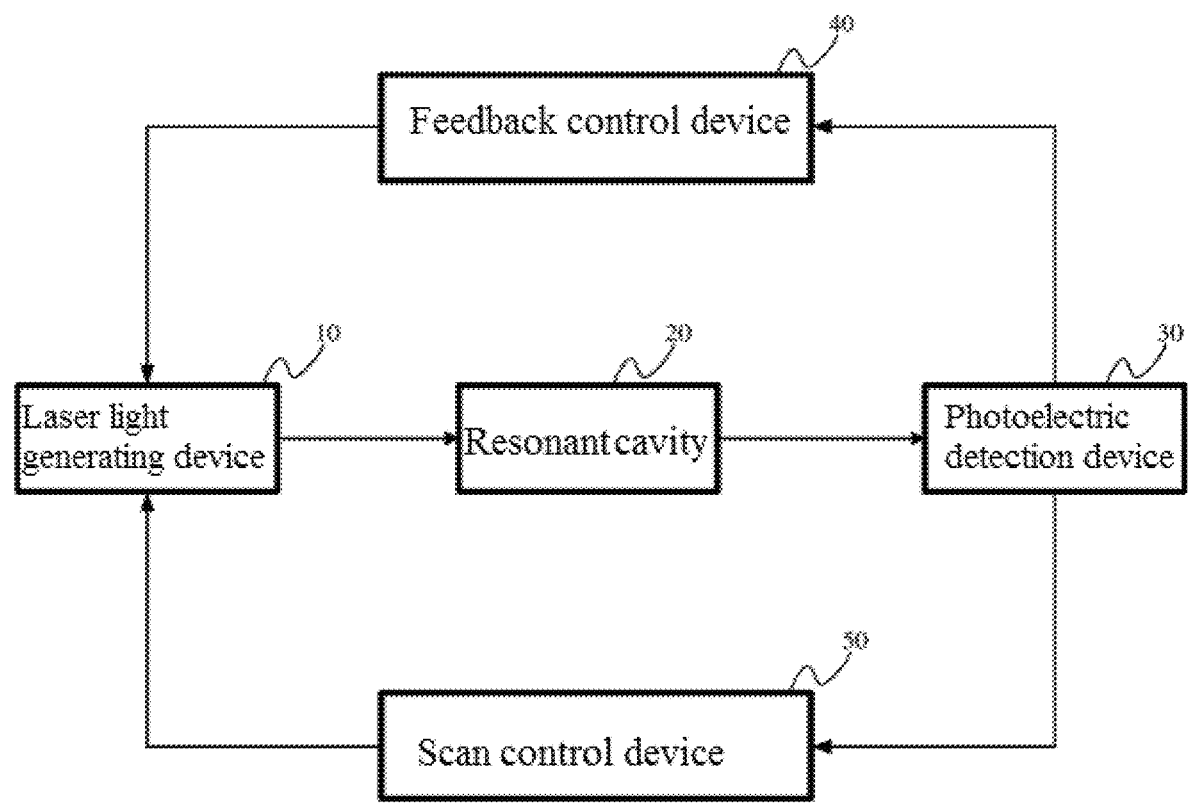
FIG. 3 is a schematic structure diagram of a system for detecting a trace gas provided by an embodiment of this application.

Hereinafter, an example of this application provides a system for detecting trace gas which enables to implement the method for detecting a trace gas. As shown in FIG. 3, the system for detecting trace gas comprises: a laser light generating device 10, a resonant cavity 20, a photoelectric detection device 30, a feedback control device 40 and a scan control device 50; wherein the cavity interior of the resonant cavity 20 is configured to fill with a gas to be tested, wherein the gas to be tested contains a trace gas to be tested; and the cavity of the resonant cavity 20 has retractable degree of freedom in the extension direction of the resonant cavity 20;

the laser light generating device 10 is configured to provide probe light with different frequencies under control of the feedback control device 40, wherein the probe light enters into interior of the resonant cavity 20 from one end of the resonant cavity 20 in an extension direction of the resonant cavity, and exits from the other end of the resonant cavity 20 in an extension direction of the resonant cavity, to capture the probe light carrying information of the trace gas to be tested;

the photoelectric detection device 30 is configured to convert the probe light carrying information of the trace gas to be tested into detection information in an electrical signal form;

the scan control device 50 is configured to record the detection information in an electrical signal form, and to control the laser light generating device 10 to adjust the frequency of the outgoing probe light in a stepping manner; and the feedback control device 40 is configured to control the frequency of the outgoing probe light from the laser light generating device 10 to match with a frequency of a longitudinal mode of the resonant cavity 20.

In this example, because the feedback control device 40 can control the frequency of the outgoing probe light from the laser light generating device 10 to match with the frequency of the longitudinal mode of the resonant cavity 20, the scan control device 50 may be only configured to control the laser light generating device 10 to adjust the frequency of the outgoing probe light in a stepping manner. When the frequency of the outgoing probe light from the laser light generating device 10 have been changed under the control of the scan control device 50, the feedback control device 40 adjusts the frequency of the longitudinal mode of the resonant cavity 20 and/or the frequency of the outgoing probe light from the laser light generating device 10 in real-time, to allow the frequency of the outgoing probe light from the laser light generating device 10 to match with the frequency of the longitudinal mode of the resonant cavity 20.

In addition, the purpose of the scan control device 50 controlling the laser light generating device 10 to adjust the frequency of the outgoing probe light in a stepping manner is to enable the scan control device 50 to record the detection information in an electrical signal form corresponding to the information of the trace gas to be tested carried by the probe light with different frequencies, so that the saturated molecular absorption spectrum of the trace gas to be tested can be obtained according to the recorded detection information in an electrical signal form, and the concentration of the trace gas to be tested in the gas to be tested can be calculated according to the saturated molecular absorption spectrum of the trace gas.

Optionally, in an example of this application, the scan control device 50 is further configured to obtain a saturated molecular absorption spectrum of the trace gas to be tested according to recorded detection information in an electrical signal form, and to calculate the concentration of the trace gas to be tested in the gas to be tested according to the saturated molecular absorption spectrum of the trace gas.

Referencing to FIG. 2, the resonant cavity 20 comprises:

a shell 21, having an incoming end and an outgoing end which are arranged opposite to each other;

a first reflector 22 located inside the shell 21 and close to the incoming end side, wherein an anti-reflection film is provided at one side of the first reflector 22 facing to the incoming end;

a second reflector 23 located inside of the shell 21 and close to the outgoing end side, wherein reflective surfaces of the first reflector 22 and the second reflector 23 are arranged opposite to each other; and a piezoelectric device arranged adjacent to the first reflector 22 and/or the second reflector 23, wherein the piezoelectric device is configured to push the first reflector 22 and/or the second reflector 23 adjacent to the piezoelectric device to move according to a received control electrical signal, to provide the cavity of the resonant cavity 20 with a retractable degree of freedom in the extension direction of the resonant cavity 20.

In this example, the cavity of the resonant cavity 20 is constructed between the first reflector 22 and the second reflector 23, so that the probe laser can obtain cavity enhancement in the cavity.

The anti-reflection film located at the side of the first reflector 22 facing the incoming end is configured to increase the transmittance of probe light incident on the first reflector 22, and to improve the light energy utilization rate of the probe light.

Optionally, the feedback control device 40 comprises: a radio-frequency signal source, a phase detection device and a PID (Proportional-Integral-Derivative) amplification device; wherein the radio-frequency signal source is configured to generate a sinusoidal radio-frequency signal;

the phase detection device is configured to convert the detection information in an electrical signal form into an error signal according to the sinusoidal radio-frequency signal; and the PID amplification device is configured to convert the error signal into a feedback locking signal, so that the frequency of the probe light exiting from the laser light generating device 10 matches with the frequency of the longitudinal mode of the resonant cavity 20.

In this example, the radio-frequency signal source in the feedback control device 40 is used to provide a reference signal for the working of the phase detection device. The phase detection device converts the detection information in an electrical signal form into the error signal. The PID amplification device converts the error signal into the feedback locking signal, and transmits it to the piezoelectric device, so that the piezoelectric device adjusts the cavity length of the resonant cavity 20 in the extension direction of the resonant cavity 20 according to the feedback locking signal, in order to adjust the frequency of the longitudinal mode of the resonant cavity 20 to match with the frequency of the probe light outgoing from the laser light generating device 10.

Correspondingly, the scan control device 50 only needs to control the laser light generating device 10 to adjust the frequency of the outgoing probe light in a stepping manner. The feedback control device 40 allows the frequency of the longitudinal mode of the resonant cavity 20 to match with the frequency of the probe light outgoing from the laser light generating device 10 by adjusting the cavity length of the resonant cavity 20.

It should to be noted that the smaller the step size change of the frequency of the probe light from the laser light generating device 10 controlled by the scan control device 50, the more accurate the concentration of the gas to be tested obtained by calculation finally. The frequency of the probe light of the laser light generating device 10 controlled by the scan control device 50 may change in the order of megahertz or in the order of hundreds of megahertz. The specific values of the step size change of the probe light and the specific range of the frequency change are not particularly limited in this application, and they may be determined depending on the actual situation.

Optionally, the laser light generating device 10 comprises: a laser, a frequency modulation device and a coupling lens;

the laser is configured to generate a laser light;

the frequency modulation device is configured to modulate the laser light generated by the laser according to the feedback locking information, to obtain probe light with a frequency matching with the frequency of the longitudinal mode of the resonant cavity 20; and the coupling lens is configured to couple the probe light and to allow coupled probe light to enter into the resonant cavity 20.

The laser may be a conventional laser, e.g., a semiconductor laser, a fiber laser or a solid-state laser. It is not particularly limited in this application, and may be determined depending on the actual situation.

Optionally, the frequency modulation device is an electro-optic modulator.

Optionally, the scan control device 50 comprise: an information storage device and a frequency scanning device, wherein the information storage device is configured to record the detection information in an electrical signal form; and the frequency scanning device is configured to generate a control electrical signal, and to transmit the control electrical signal to the laser.

In this example, the scan control device 50 controls the frequency of the laser light generated by the laser to change in a certain step size.

Optionally, the photoelectric detection device 30 comprises a lens matching module and a photoelectric detection module, wherein the lens matching module is configured to match the spatial pattern of a light field inside the photoelectric detection device 30; and the photoelectric detection module is configured to convert the probe light carrying information of the trace gas to be tested into the detection information in an electrical signal form.

The specific implementation effects of the system for detecting trace gas provided by an embodiment of this application is illustrated below in conjunction with specific examples.

In this example, the trace gas to be tested was $^{12}C^{16}O$ gas molecules. The purpose was to measure saturated molecular absorption spectroscopy of the infrared vibrational transition of the $^{12}C^{16}O$ gas molecules, and to obtain the gas partial pressure of the $^{12}C^{16}O$ gas molecules according to the peak area.

Optionally, the laser was an external-cavity semiconductor laser. Its output laser light was modulated by an electro-optic modulator and coupled by a coupling lens before entering into the resonant cavity 20. The interior of the resonant cavity 20 was filled with the gas to be tested containing the $^{12}C^{16}O$ gas. The total pressure of the gas to be tested was P, which was measured by a pressure gauge connected with the resonant cavity 20. The resonant cavity 20 was provided with the first reflector 22 and the second reflector 23, and the reflectivity of the first reflector 22 and the second reflector 23 were up to 99.995%. The first reflector 22 and the second reflector 23 constitutes an optical resonant cavity 20. The back surfaces of the first reflector 22 or the second reflector 23 were connected with a piezoelectric device, which was capable of driving the lens to move slightly along the optical path (extension direction of the resonant cavity 20).

The probe light carrying information of the trace gas to be tested outgoing from the resonant cavity 20 was converted into the detection information in an electrical signal form by the photoelectric detection device 30. After the detection signals in an electrical signal form were amplified by filtering, it was divided into two groups of signals, in which one group of signals was sent into the feedback control device 40, and produced a feedback locking signal after being demodulated by the feedback control device 40, so that the frequency of a longitudinal mode of the resonant cavity 20 matched with the frequency of the outgoing probe light from the laser light generating device 10; the other group of signals was sent to the scan control device 50 and recorded, meanwhile the scan control device 50 controlled the laser light generating device to do frequency scanning in a stepping manner.

Figure 4:
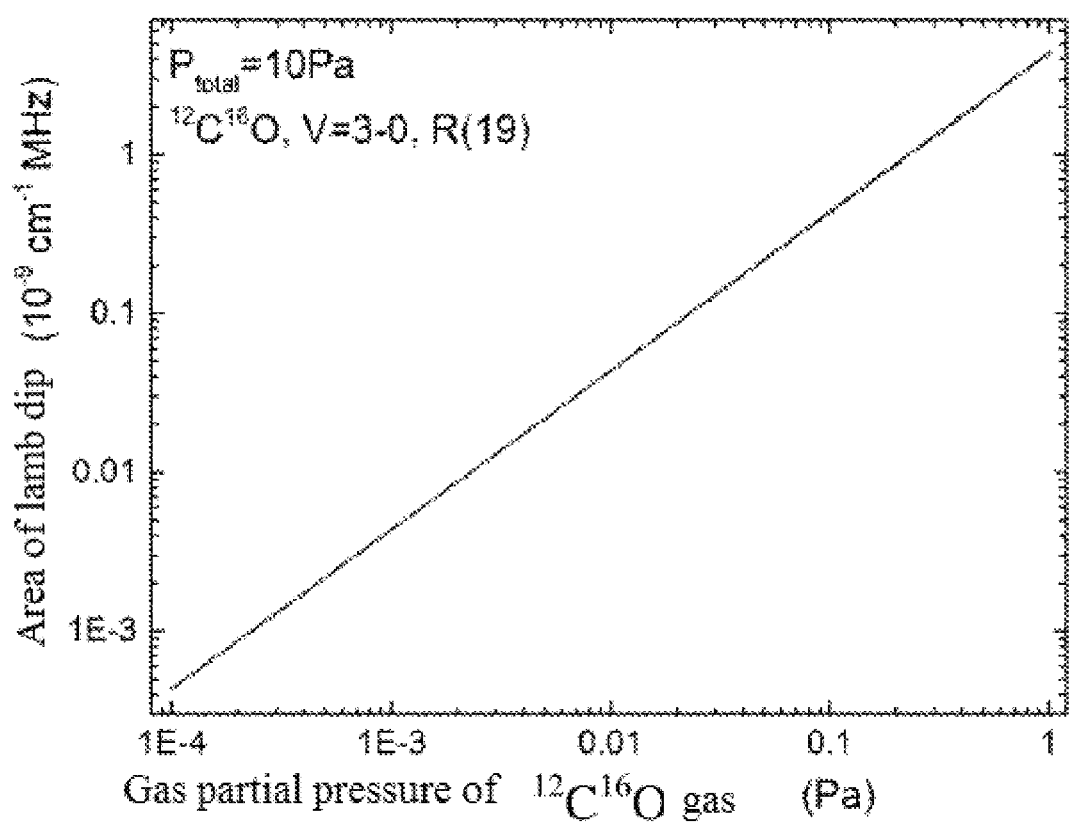
FIG. 4 is a drawing showing the relationship between the partial pressure of the trace gas to be tested ($^{12}C^{16}O$) in the gas to be tested and the Lamb dip area of R(19) transition thereof obtained by simulation.
Figure 5:
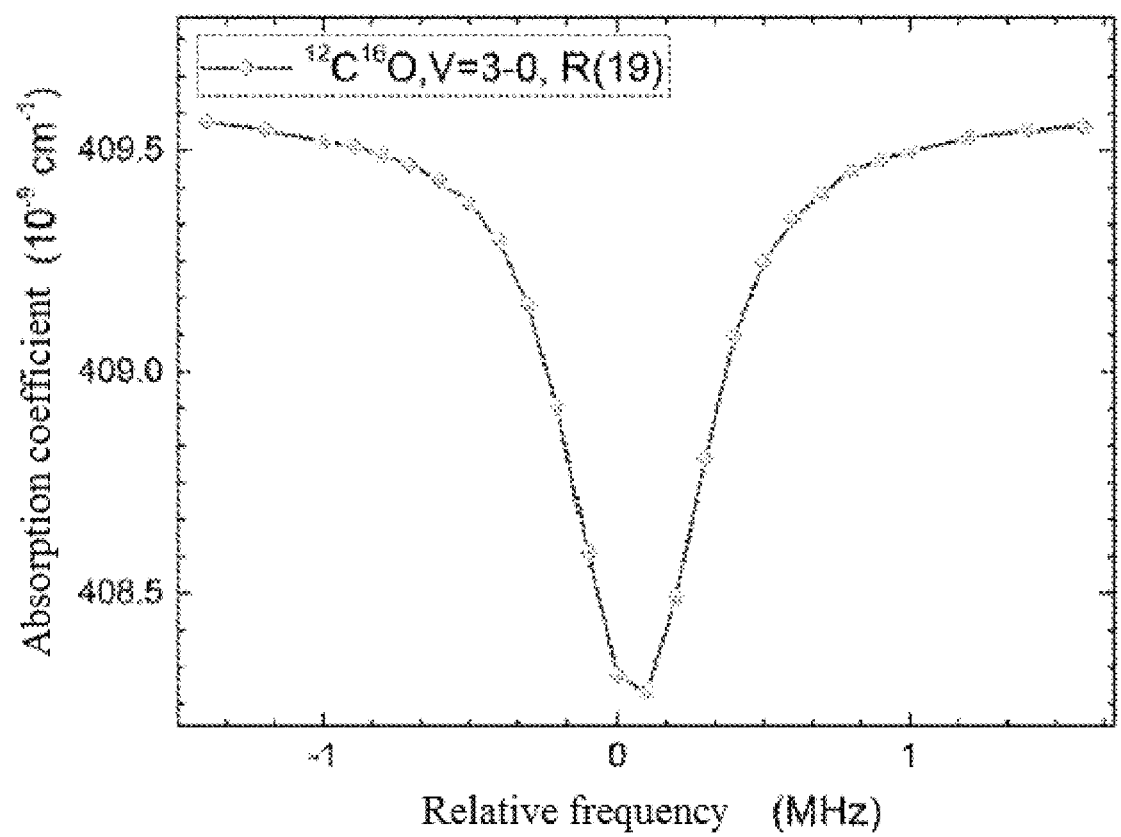
FIG. 5 is a measured saturated molecular absorption spectrum of cavity enhanced molecular R(19) transition at V=3–0.

Through the above scanning process of the probe laser, the saturated molecular absorption spectrum of the trace gas to be tested was obtained. Referencing to FIG. 4 and FIG. 5, FIG. 4 is a drawing showing the relationship between the partial pressure of the trace gas to be tested ($^{12}C^{16}O$) in the gas to be tested and the Lamb dip area of R(19) transition thereof obtained by simulation, in which the abscissa of FIG. 4 is the partial pressure of the $^{12}C^{16}O$ gas in a unit of Pascal (Pa), and the ordinate is the area of Lamb dip in a unit of $10^{-9}$ cm$^{-1}$ MHz. FIG. 5 is a measured saturated molecular absorption spectrum of cavity enhanced molecular R(19) transition at V=3-0, in which the abscissa of FIG. 5 is relative frequency in a unit of megahertz (MHz); and the ordinate is absorption coefficient in a unit of $10^{-9}$ cm$^{-1}$. It can be seen from FIG. 4 that the partial pressure of the trace gas to be tested ($^{12}C^{16}O$) and the Lamb dip area of R(19) transition thereof have a good corresponding linear relationship in a wide range, which is suitable for quantitative measurement. By fitting the saturated molecular absorption spectrum shown in FIG. 5, peak height, peak width and peak area thereof were obtained, so that the partial pressure of the trace gas to be tested ($^{12}C^{16}O$) in the gas to be tested was determined.

In summary, the embodiments of this application provide a method and a system for detecting a trace gas. In the method for detecting a trace gas, the gas to be tested is filled into the resonant cavity. On one hand, the resonant cavity enhances the laser power of the probe light entering into the resonant cavity to improve the saturation parameters of molecular transition of the trace gas to be tested, and on the other hand enhances the effective absorption range of the trace gas to be tested, so that the sensitivity for detecting the weak absorption of the trace gas to be tested is increased and the saturated molecular absorption spectrum of the trace gas to be tested is obtained, which realizes the purpose of detecting the concentration of a trace gas by using the probe light supplied by a conventional laser under normal temperature condition.

In addition, due to the Doppler-free broadening property of the saturated molecular absorption spectrum, the obtained saturated molecular absorption spectrum of the trace gas to be tested may be effectively separated from the absorption spectra of the background gas molecules in the gas to be tested, thereby eliminating the interference from the background gas, and realizing the detection of the trace gas to be tested. Since frequencies of the saturated absorption spectra of the different molecular isotopes are significantly different, the method for detecting the trace gas provided by the embodiment of this application is also particularly effective for detecting a molecule with a specific isotope.

In this specification, the various examples are described in a progressive manner. Each embodiment focuses on its differences from other embodiments, and the same or similar parts between the various embodiments can be referred to each other.

Based on the above description of the disclosed examples, those skilled in the art can implement or carry out the present disclosure. It is apparent for those skilled in the art to make many modifications to these examples. The general principle defined herein may be applied to other examples without departing from the spirit or scope of the present disclosure. Therefore, the present disclosure is not limited to the examples illustrated herein, but should conform to the widest scope consistent with the principle and novel features disclosed herein.

The invention claimed is:

1. A system for detecting a trace gas, comprising:
a laser light generating device, a resonant cavity, a photoelectric detection device, a feedback control device and a scan control device; wherein
the cavity interior of the resonant cavity is configured to fill with a gas to be tested, wherein the gas to be tested contains a trace gas to be tested; and the cavity of the resonant cavity has retractable degree of freedom in the extension direction of the resonant cavity;
the laser light generating device is configured to provide probe light with different frequencies under control of the feedback control device, wherein the probe light enters into interior of the resonant cavity from one end of the resonant cavity in an extension direction of the resonant cavity, and exits from the other end of the resonant cavity in an extension direction of the resonant cavity, to capture the probe light carrying information of the trace gas to be tested;

the photoelectric detection device is configured to convert the probe light carrying information of the trace gas to be tested into detection information in an electrical signal form;

the scan control device is configured to record the detection information in an electrical signal form, and to control the laser light generating device to adjust frequency of outgoing probe light in a stepping manner; and the feedback control device is configured to control the frequency of the outgoing probe light from the laser light generating device to match with a frequency of a longitudinal mode of the resonant cavity; wherein the feedback control device comprises: a radio-frequency signal source, a phase detection device and a PID amplification device; wherein the radio-frequency signal source is configured to generate a sinusoidal radio-frequency signal;

the phase detection device is configured to convert the detection information in an electrical signal form into an error signal according to the sinusoidal radio-frequency signal; and the PID amplification device is configured to convert the error signal into a feedback locking signal, so that the frequency of the probe light exiting from the laser light generating device matches with the frequency of the longitudinal mode of the resonant cavity.

2. The system according to claim 1, wherein the resonant cavity comprises:

a shell, having an incoming end and an outgoing end which are arranged opposite to each other;

a first reflector located inside the shell and close to the incoming end side, wherein an anti-reflection film is provided at one side of the first reflector facing to the incoming end;

a second reflector located inside of the shell and close to the outgoing end side, wherein reflective surfaces of the first reflector and the second reflector are arranged opposite to each other; and a piezoelectric device arranged adjacent to the first reflector and/or arranged adjacent to the second reflector, wherein the piezoelectric device is configured to push the first reflector and/or the second reflector adjacent to the piezoelectric device to move according to a received control electrical signal, to provide the cavity of the resonant cavity with a retractable degree of freedom in the extension direction of the resonant cavity.

3. The system according to claim 1, wherein the laser light generating device comprises a laser, a frequency modulation device, and a coupling lens:

the laser is configured to generate a laser light;

the frequency modulation device is configured to modulate the laser light generated by the laser according to the feedback locking information, to obtain probe light with a frequency matching with the frequency of the longitudinal mode of the resonant cavity; and the coupling lens is configured to couple the probe light and then to allow the coupled probe light to enter into the resonant cavity.

4. The system according to claim 3, wherein the frequency modulation device is an electro-optic modulator.

5. The system according to claim 2, wherein the scan control device comprises an information storage device and an frequency scanning device, wherein the information storage device is configured to record the detection information in an electrical signal form; and the frequency scanning device is configured to generate a control electrical signal, and to transmit the control electrical signal to the laser.

6. The system according to claim 1, wherein the scan control device is further configured to obtain a saturated molecular absorption spectrum of the trace gas to be tested according to recorded detection information in an electrical signal form, and to calculate the concentration of the trace gas to be tested in the gas to be tested according to the saturated molecular absorption spectrum of the trace gas.

7. The system according to claim 1, wherein the photoelectric detection device comprises a lens matching module and a photoelectric detection module, wherein the lens matching module is configured to match the spatial pattern of a light field inside the photoelectric detection device; and the photoelectric detection module is configured to convert the probe light carrying information of the trace gas to be tested into the detection information in an electrical signal form.

8. A method for detecting a trace gas, comprising using the system according to claim 1.

* * * * *